United States Patent
Jandhyala et al.

(10) Patent No.: US 11,156,586 B2
(45) Date of Patent: Oct. 26, 2021

(54) DETERMINING NON-PLASTIC STATE SHRINKAGE IN A CEMENT SLURRY

(71) Applicant: HALLIBURTON ENERGY SERVICES, INC., Houston, TX (US)

(72) Inventors: Siva Rama Krishna Jandhyala, Pune (IN); Shanu Jain, Pune (IN); Ganesh Pangu, Dabhade (IN)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 108 days.

(21) Appl. No.: 16/634,951

(22) PCT Filed: Nov. 10, 2017

(86) PCT No.: PCT/US2017/061061
§ 371 (c)(1),
(2) Date: Jan. 29, 2020

(87) PCT Pub. No.: WO2019/094025
PCT Pub. Date: May 16, 2019

(65) Prior Publication Data
US 2020/0240955 A1    Jul. 30, 2020

(51) Int. Cl.
*G01N 29/024* (2006.01)
*G01N 33/38* (2006.01)
*E21B 47/005* (2012.01)

(52) U.S. Cl.
CPC ......... *G01N 29/024* (2013.01); *E21B 47/005* (2020.05); *G01N 33/383* (2013.01); *G01N 2291/028* (2013.01); *G01N 2291/0232* (2013.01)

(58) Field of Classification Search
CPC ................. G01N 29/024; G01N 29/07; G01N 2291/0232; G01N 2291/028;
(Continued)

(56) References Cited

U.S. PATENT DOCUMENTS

| 4,259,868 A | 4/1981 | Rao et al. |
| 5,741,971 A | 4/1998 | Lacy |

(Continued)

FOREIGN PATENT DOCUMENTS

WO    WO2016/186653 A1    11/2016

OTHER PUBLICATIONS

International Search Report and Written Opinion issued for Application No. PCT/US2017/061061, dated Jan. 11, 2018, ISA/KR, 10 pages.

(Continued)

*Primary Examiner* — Suman K Nath
(74) *Attorney, Agent, or Firm* — Haynes and Boone, LLP

(57) ABSTRACT

A system and method to determine a non-plastic state shrinkage (NPSS) characteristic of a cement slurry. The system and method can include operations of transmitting an ultrasonic signal through the slurry, recording a transit time of the ultrasonic signal as the slurry cures, plotting the transit time, measuring and plotting a shrinkage of the slurry, determining a transition of the transit time from an increased rate of change to a decreased rate of change, determining a first curing time at the transition, determining the detected volume at the first curing time based on the second plot; and determining a change in the detected volume from the first curing time to a second curing time, wherein the second curing time is after the first curing time.

19 Claims, 7 Drawing Sheets

(58) Field of Classification Search
CPC .......... G01N 2291/02818; G01N 2291/02854; G01N 33/383; E21B 47/005
See application file for complete search history.

(56) References Cited

U.S. PATENT DOCUMENTS

| | | | |
|---|---|---|---|
| 6,383,420 B1 * | 5/2002 | Mohr | B28B 7/0005 264/39 |
| 6,819,121 B1 * | 11/2004 | Hager, III | G01N 33/383 324/664 |
| 7,380,466 B2 | 6/2008 | Deeg | |
| 2009/0194330 A1 * | 8/2009 | Gray | E21B 21/00 175/24 |
| 2016/0238586 A1 | 8/2016 | Services | |

OTHER PUBLICATIONS

Biot, M.A., "Theory of Propagation of Elastic Waves in a Fluid-Saturated Porous Solid," J. Appl. Phys. 28, 2, pp. 168-178 (1956).

Hammer, T.A., "Is There a Relationship Between Pore Water Pressure and Autogenous Shrinkage Before and During Setting?" Self-Desiccation and Its Importance in Concrete Technology, Edited by B. Persson and G. Fagerlund, Report TVBM-3104, Division of Building Materials, Lund Institute of Technology, Proceedings of the Third International Research Seminar in Lund, pp. 27-38, (2002).

Reddy, B. R., Ying XU, Kris Ravi, Dennis Gray, Pattillo, P. D.: "Cement Shrinkage Measurement in Oilwell Cementing—A Comparative Study of Laboratory Methods and Procedures", SPE 103610, 2007, presented at SPE Rocky Mountain Oil & Gas Technology Symposium, Denver, Colorado, Apr. 16-18.

Sayers, C.M. & Grenfell, R.L., "Ultrasonic propagation through hydrating cements," Ultrasonics, 31, 3, pp. 147-153 (1993).

Gaurav Sant, Pietro Lura, Jason Weiss; "Measurement of Volume Change in Cementitious Materials at Early Ages: Review of Testing Protocols and Interpretation of Results," Transportation Research Board, Nov. 14, 2005.

* cited by examiner

DETERMINING NON-PLASTIC STATE SHRINKAGE IN A CEMENT SLURRY

CROSS-REFERENCE TO RELATED APPLICATION

The present application is a U.S. National Stage patent application of International Patent Application No. PCT/US2017/061061, filed on Nov. 10, 2017, the benefit of which is claimed and the disclosure of which is incorporated herein by reference in its entirety.

TECHNICAL FIELD

The present disclosure generally relates to determining stresses that can develop in cement used to secure a tubing string (such as casing) in a wellbore. More particularly still, the present disclosure relates to methods and systems for estimating stresses in a cement slurry that may occur in a wellbore as the cement slurry cures by collecting shrinkage data of a cement slurry with a particular composition, such as plastic and non-plastic state shrinkage data, and inputting the shrinkage data for the composition into a simulation tool, which can determine the estimated stresses for the particular cement slurry composition, based on the shrinkage data.

BACKGROUND

Wellbores exist in extremely dynamic environments; therefore, a cement sheath may be required to perform as intended for an extended period of time. When cementing a well, a primary concern can be to prevent fluids from migrating into an annulus. As a well ages, the annular seal may be compromised as a result of stresses brought on by temperature and pressure cycling that occur as the well is operated. Micro-annuli or small cracks can be formed, which may allow annular pressure buildup, water influx or a loss of hydrocarbons.

The oil and gas industry may have traditionally focused on the short-term properties that apply when the cement is still in its liquid slurry form and during the first 24 hours after placement. By industry convention and tradition, the effect of stresses on the cement sheath's mechanical properties may not be assessed during the design and construction phase of a well. Although short term considerations are necessary for effective slurry mixing and placement, a focus on liquid cement slurry properties and the 24 hour compressive strength may not account for long-term cement integrity.

Regardless of when it occurs during the life of the well, a loss in cement sheath integrity can result in the loss of zonal isolation, thus creating a path for formation fluids to enter the annulus. This migration of fluids can ultimately pressurize the well and potentially render it unsafe to operate. A failure in the cement sheath can also possibly cause premature and unwanted water production, which can limit the economic life of the well. When the cement sheath integrity has been compromised, operators can attempt to work over the well to remediate the problem. However, repairs may be difficult, costly and in most cases impractical; therefore, it can be more economical in the long run to address cementing issues during the original cement job to avoid the substantially higher remediation costs and the loss of production due to down time or even having to resort to shutting the well altogether.

A computer simulation software for the planning and design phase (such as WELLLIFE™ software used by Halliburton Energy Services, Inc.) may help to optimize the life of the well by analyzing and evaluating the various short-term and long-term properties of a cement sheath. The computer simulation software can include simulation models that evaluate key parameters such as: material properties of various cements, cement placement during the completion process, and changes in the well due to various operational stresses that in turn can damage the cement sheath. In short, the computer simulation software models cement sheath integrity and the variables that may introduce risk of its failure as it is subjected to different well conditions. The information given by this modeling can aid in the development of a cement slurry composition that can meet the unique properties required by a particular well for long-term zonal isolation when it is cured into cement downhole.

The computer simulation software can use finite element analysis to evaluate mechanical properties, such as Young's modulus, friction angle, cohesion of the set cement, and simulate failure events that could occur during various field operations to help determine optimum mechanical properties for better sheath integrity for the life of the well. Simulated failure modes can include debonding, cracking, and plastic deformation. Tensile strength experiments, unconfined and confined tri-axial experimental tests, hydrostatic tests and uniaxial (Oedometer) tests can help characterize the material behavior of different cement types.

Some of the parameters needed as inputs to the computer simulation software are the characteristics of a cement slurry, which the software can use to simulate the performance of the particular cement slurry in a particular well environment. At least one of these parameters is the shrinkage. Any shrinkage of hydrating cement first progresses through a plastic state shrinkage (PSS) regime and then enters a non-plastic state shrinkage (NPSS) regime. NPSS is the shrinkage that occurs after cement slurry has built a finite solid skeleton and starts to become load bearing. The plastic state shrinkage (PSS) is the shrinkage that occurs in the cement slurry while the cement slurry remains in a liquid form and gel form, and thus prevents stresses (due to shrinkage) from developing in the cement slurry. NPSS is the shrinkage that occurs after a solid structure in the cement slurry forms, due to which stresses can develop in the cement slurry. Therefore, NPSS is a desired parameter for use in calculating stresses in the cement slurry as it cures. Subsequently, PSS is from any measured shrinkage before it can be used in design software to predict stresses developed in cement sheath. This means, it is mandatory to not just measure shrinkage vs. time but also to identify when NPSS begins (or PSS ends). With the information of both measured shrinkage vs. time and the end time of PSS, the amount of shrinkage that occurs during NPSS can be determined by subtracting the amount of shrinkage that occurred during PSS from the measured shrinkage.

Two tests are generally performed to determine the beginning of NPSS of the cement slurry. One test determines the bulk shrinkage and the other test determines the total shrinkage. While the bulk and total shrinkage values are equal, the cement slurry is in a plastic state shrinkage phase. When the bulk and total shrinkage values begin to diverge from each other, then the cement slurry is in the non-plastic state shrinkage (NPSS) phase. Total and bulk shrinkage tests are generally performed separately from each other and care must be taken to produce, as much as possible, the same environmental conditions in each test to minimize errors in the results. Varied environmental conditions in either test can cause errors and inaccuracies in the measurements and thereby propagate errors into the identification of the beginning of NPSS and thus the amount of shrinkage that should be used in stress calculations of the cement slurry.

Therefore, it can readily be appreciated that improvements in the arts of determining the beginning of NPSS of cement slurries along with the complete shrinkage vs. time are continually needed.

BRIEF DESCRIPTION OF THE DRAWINGS

Various embodiments of the present disclosure will be understood more fully from the detailed description given below and from the accompanying drawings of various embodiments of the disclosure. In the drawings, like reference numbers may indicate identical or functionally similar elements. Embodiments are described in detail hereinafter with reference to the accompanying figures, in which.

DETAILED DESCRIPTION OF THE DISCLOSURE

Figure 1:
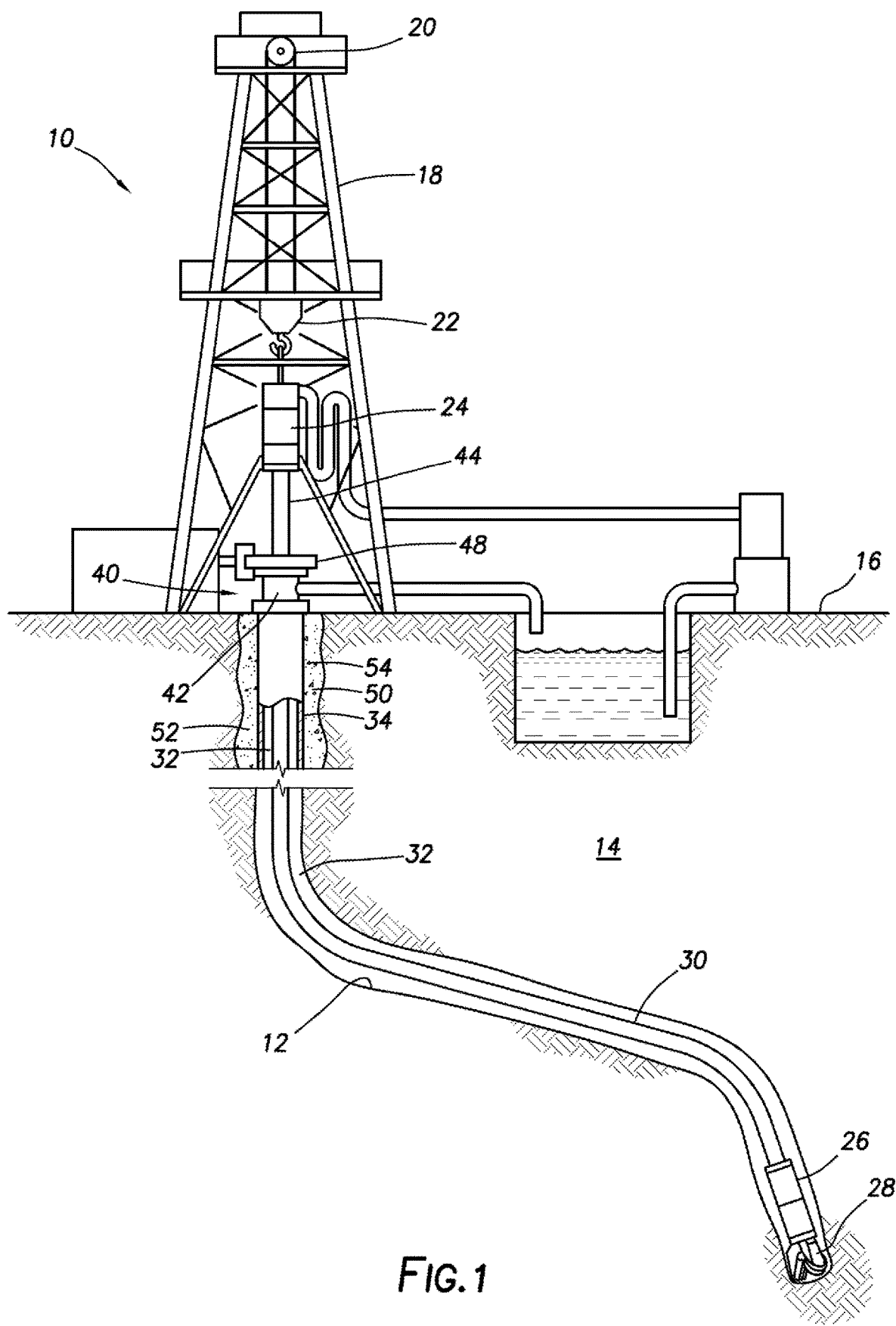
FIG. 1 is a representative partial cross-sectional view of a wellbore system with a cased portion of a drilled wellbore including a cement sheath that can benefit from the principles of this disclosure, according to one or more example embodiments.

The disclosure may repeat reference numerals and/or letters in the various examples or Figures. This repetition is for the purpose of simplicity and clarity and does not in itself dictate a relationship between the various embodiments and/or configurations discussed. Further, spatially relative terms, such as beneath, below, lower, above, upper, uphole, downhole, upstream, downstream, and the like, may be used herein for ease of description to describe one element or feature's relationship to another element(s) or feature(s) as illustrated, the upward direction being toward the top of the corresponding figure and the downward direction being toward the bottom of the corresponding figure, the uphole direction being toward the surface of the wellbore, the downhole direction being toward the toe of the wellbore. Unless otherwise stated, the spatially relative terms are intended to encompass different orientations of the apparatus in use or operation in addition to the orientation depicted in the Figures. For example, if an apparatus in the Figures is turned over, elements described as being "below" or "beneath" other elements or features would then be oriented "above" the other elements or features. Thus, the exemplary term "below" can encompass both an orientation of above and below. The apparatus may be otherwise oriented (rotated 90 degrees or at other orientations) and the spatially relative descriptors used herein may likewise be interpreted accordingly.

As used herein, the words "comprise," "have," "include," and all grammatical variations thereof are each intended to have an open, non-limiting meaning that does not exclude additional elements or steps. While compositions and methods are described in terms of "comprising," "containing," or "including" various components or steps, the compositions and methods also can "consist essentially of" or "consist of" the various components and steps. It should also be understood that, as used herein, "first," "second," and "third," are assigned arbitrarily and are merely intended to differentiate between two or more objects, etc., as the case may be, and does not indicate any sequence. Furthermore, it is to be understood that the mere use of the word "first" does not require that there be any "second," and the mere use of the word "second" does not require that there be any "first" or "third," etc.

The terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent(s) or other documents that may be incorporated herein by reference, the definitions that are consistent with this specification should be adopted.

Generally, this disclosure provides a system and method to determine a non-plastic state shrinkage (NPSS) characteristic of a cement slurry. The method can include operations of filling a container with the cement slurry, positioning a transmitter at an end of the container, positioning a receiver at an opposite end of the container, transmitting an ultrasonic signal through the cement slurry from the transmitter to the receiver, recording a transit time of the ultrasonic signal through the cement slurry as the cement slurry cures, plotting a first plot of the transit time vs. a curing time of the cement slurry, and maintaining the cement slurry at a constant pressure by injecting a fluid into the container, thereby compensating for shrinkage of the cement slurry as the cement slurry cures. The method can further include the operation of detecting a volume of the fluid injected into the container as the cement slurry cures, plotting a second plot of the detected volume vs. the curing time of the cement slurry, determining a first slope of the first plot that indicates an increased rate of change in the transit time and a second slope of the first plot that indicates a decreased rate of change in the transit time, determining a first curing time at which the first slope intersects the second slope, determining the detected volume at the first curing time based on the second plot; and determining a change in the detected volume from the first curing time to a second curing time, wherein the second curing time is after the first curing time.

FIG. 1 shows an elevation view in partial cross-section of a wellbore system 10 which can be utilized to drill a wellbore 12 for production of hydrocarbons and/or other fluids. Wellbore 12 can extend through various earth strata in an oil and gas formation 14 located below the earth's surface 16. Wellbore system 10 can include a rig (or derrick) 18 and a wellhead 40. The rig 18 can include a hoisting apparatus 20, a travel block 22, and a swivel 24 for raising and lowering casing, or other types of conveyance vehicles 30 such as drill pipe, coiled tubing, production tubing, and other types of pipe or tubing strings, such as wireline, slickline, and the like. In FIG. 1, the conveyance vehicle 30 is a substantially tubular, axially extending drill string, formed of a plurality of pipe joints coupled together end-to-end supporting a bottom hole assembly (BHA) 26 and a drill bit 28. However, it should be understood that the conveyance vehicle 30 can be any of the other suitable conveyance vehicles, such as those mentioned above. The rig 18 can also include a kelly 44, a rotary table 48, and other equipment (not shown) associated with rotation and/or translation of the conveyance vehicle 30 within the wellbore 12.

The wellbore system 10 in FIG. 1 is shown as an onshore system, but the system 10 can also be an offshore system. Such a system 10 can have a rig 18 mounted on an oil or gas platform, and/or semi-submersibles, drill ships, and the like (not shown). One or more subsea conduits or risers can extend from the platform to a subsea wellhead 40. The tubing string 30 can extend down from rig 18, through subsea conduits, through the wellhead 40, and into wellbore 12. However, if the wellbore system 10 is an onshore system, as in FIG. 1A, then subsea conduits may not be necessary. Wellbore 12 may be formed of single or multiple bores, extending into the formation 14, and disposed in any orientation (e.g. vertical, inclined, horizontal, combinations of these, etc.). The wellbore system 10 can also include multiple wellbores 12 with each wellbore 12 having single or multiple bores. The rig 18 may be proximate the wellhead 40, as shown in FIG. 1, or spaced apart from a wellhead 40, as in an offshore arrangement. One or more pressure control devices 42, blowout preventers (BOPs), and other equipment associated with drilling or producing a wellbore 12 can also be provided in the system 10. The wellbore system 10 can utilize a cement slurry 50 to cement a casing string 34 in a wellbore 12 and produce a cement sheath 52, when cured, that fills an annulus 54 between the casing string 34 and the wellbore 12.

As stated previously, it is beneficial to design the cement slurry for the particular environment so the integrity of the resulting cement sheath can last for many years if not decades. Therefore, a simulation of how stress develops in the cement slurry can be used to estimate (i.e. predict) the stresses that may develop in a similar cement slurry injected in a particular wellbore environment.

Figure 2:
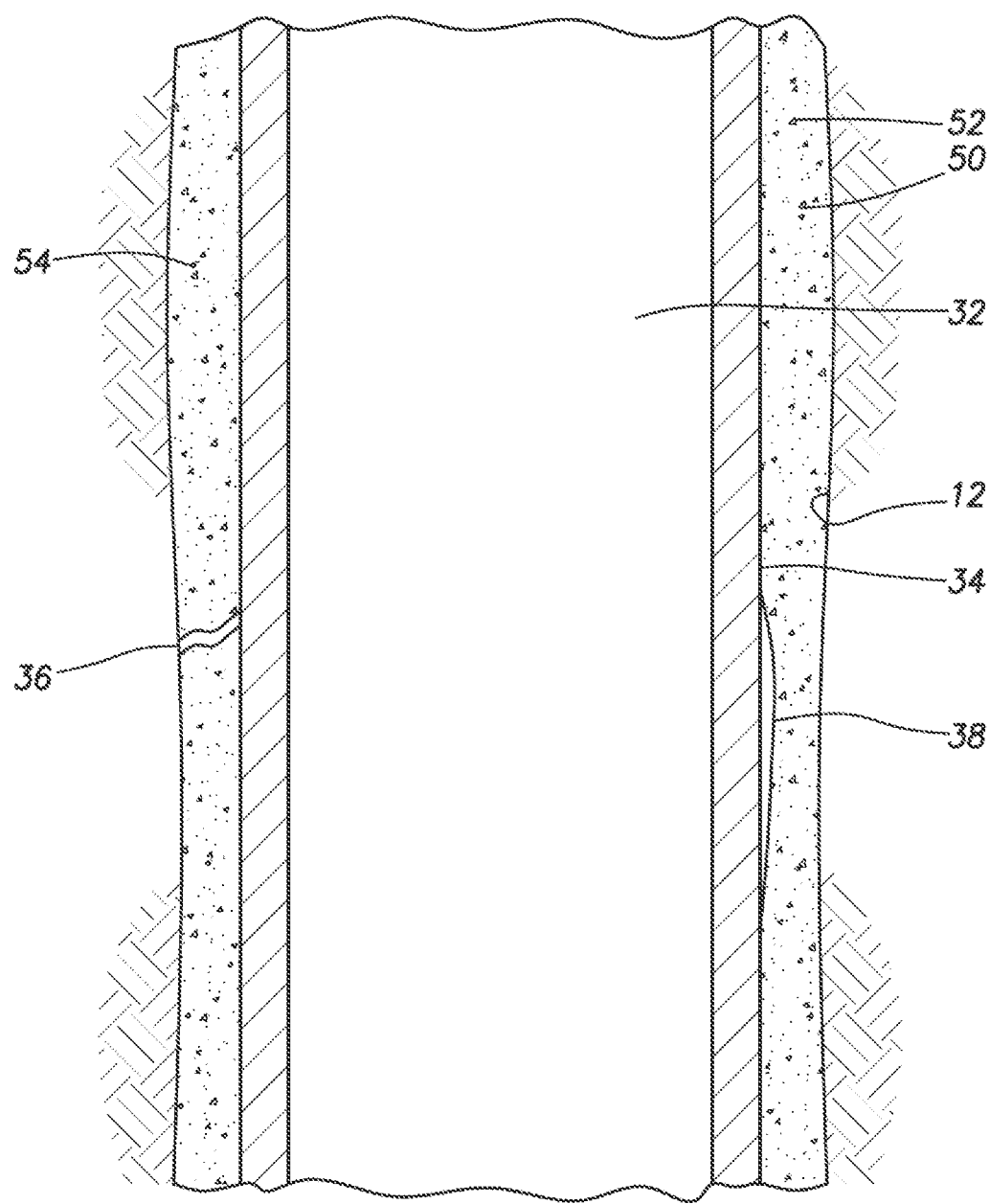
FIG. 2 is a representative partial cross-sectional view of the cased portion of the drilled wellbore of FIG. 1 with the cement sheath that can benefit from the principles of this disclosure, according to one or more example embodiments.

Referring to FIG. 2, an enlarged view of a representative cased portion of the wellbore 12 is shown with the tubing string 30 removed from the wellbore 12. As can be seen, the casing string 34 has been cemented in the wellbore 12 by the cement slurry 50 to form the cement sheath 52 in the annulus 54. Over time, the stresses (either internal and/or external) can cause damage to the cement sheath 52, such as a debonded region 38 and/or cracks 36 in the cement sheath. One way these damages can be minimized is to design the composition of the cement slurry 50 so that it creates minimal stresses in the cement sheath as the cement slurry 50 cures and ages. The current disclosure provides an improved method for determining one or more parameters of the cement slurry 50 that can be input into the simulation tool 46 to better determine and/or predict the stresses that can build up in the cement sheath 52 as the cement slurry 50 is cured downhole. The resulting parameters can enable optimization of the cement slurry compositions for long-term performance in a particular wellbore environment.

Figure 3:
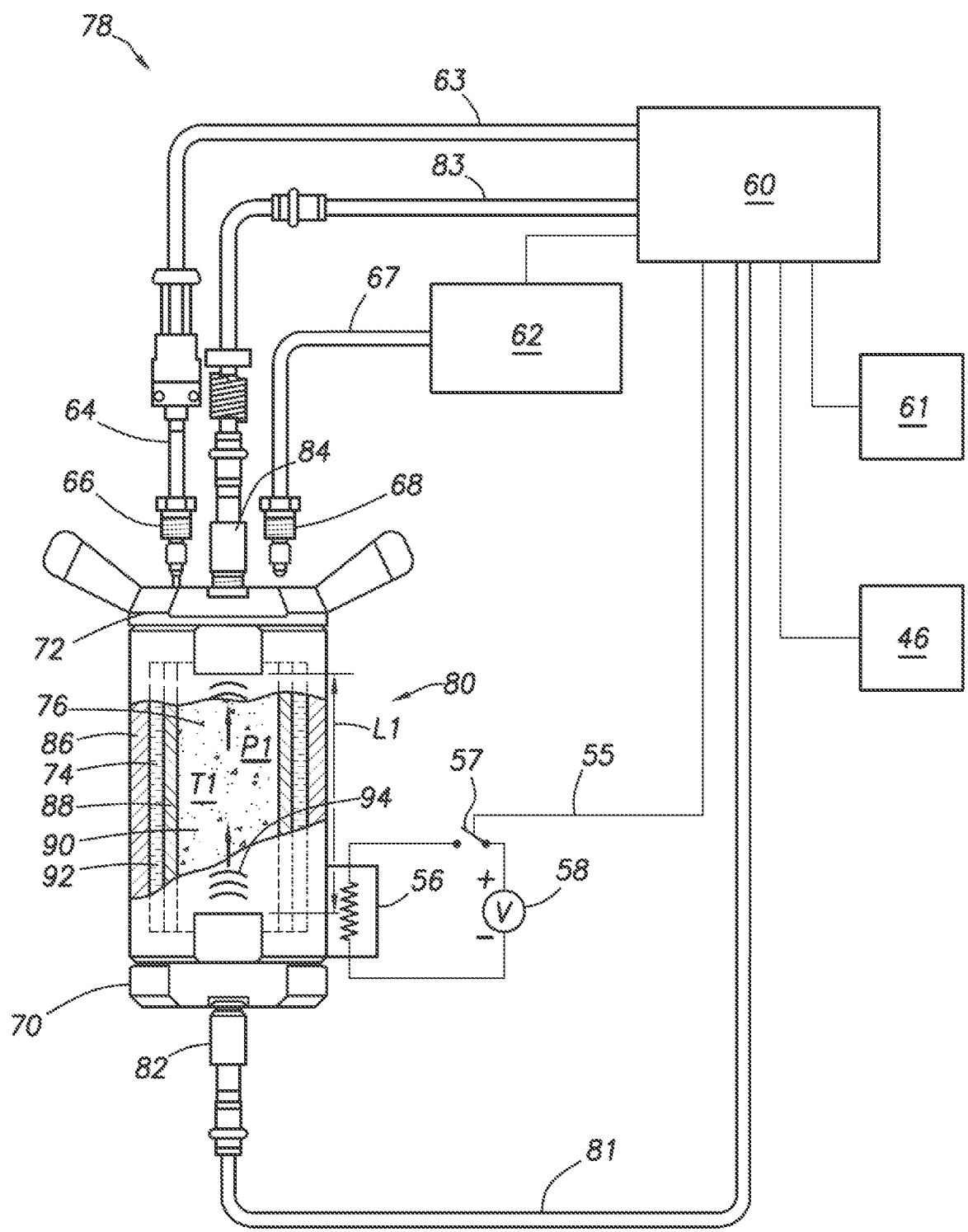
FIG. 3 is a representative partial cross-sectional view of a test setup for evaluating a cement slurry as it goes through a curing process, according to one or more example embodiments.

FIG. 3 shows an ultrasonic cement analyzer (UCA) 78 that can provide a non-destructive method for determining the relative strength development of a sample 90 of the cement slurry 50 under representative downhole temperature T1 and pressure P1 conditions. The theory of operation is based on the correlation between ultrasonic pulse velocity (or transit time) in the sample and its compressive strength. Strength indications are determined by measuring the change in velocity of an ultrasonic signal transmitted through the cement sample as it cures. The current disclosure uses the UCA 78 to record a transit time of the ultrasonic pulse (or signal) through the sample 90 of the cement slurry 50 as the sample 90 cures. As used herein, "transit time" is the time it takes for the ultrasonic signal to travel from an ultrasonic transmitter 82, through the sample 90, and to an ultrasonic receiver 84. The velocity of the ultrasonic signal 94 can be determined by dividing the transit time by the distance L1, which is the distance between the transmitter 82 and the receiver 84. This transit time varies as the solidity of the sample 90 changes during the curing process.

The UCA 78 can include a processor 60, which may include one or more processors. The processor 60 can be coupled to the ultrasonic transmitter 82 via the control line 81 and to the ultrasonic receiver 84 via the control line 83. The processor 60, via the control line 81, can control the transmitter 82 to transmit ultrasonic signals 94 into the sample 90 of the cement slurry 50. The processor 60, via the control line 83, can control the receiver 84 to receive the ultrasonic signals 94 from the sample 90 and have the receiver 84 communicate the received signal data to the processor 60 which can process the received signal data to determine the transit time of the signals 94 through the sample 90. The processor 60 can plot the transit times as a function of the curing time to provide a plot curve 120 (see FIG. 4) of the transit times vs. curing time of the sample 90 and display the plot curve 120 to a user via a display unit 61.

The processor 60 can control the temperature T1 in the chamber 80, by controlling a heater 56. The heater 56 can be switched OFF and ON via the control line 55 and switch 57, which selectively applies the voltage potential V from the power supply 58 to the heater 56. A thermocouple 64 can measure the temperature T1 in the chamber 80 and present the temperature measurements to the processor 60 via control line 63 so that the processor 60 can control the heater 56 as needed to increase or allow a decrease of the temperature T1 in the chamber 80. It should be understood that one of ordinary skill in the art will recognize many other possible configurations of a heater 56 that can be used in keeping with the principles of this disclosure, as long as the heater (or other heat source) 56 can be controlled to maintain a substantially constant temperature T1 in the interior 76 of the tube 88, and where the substantially constant temperature T1 can be representative of a temperature downhole in a particular wellbore 12 or earthen formation 14. As used herein "substantially constant" temperature or pressure is defined as a temperature or pressure that is held within +/−10% of the desired temperature or pressure.

The pressurization unit 62 can be controlled by the processor 60 to maintain a substantially constant pressure P1 in the interior 76 of the tube 88. The pressurization unit 62 can include a precision pump that can inject/extract amounts of fluid (such as water) to/from the interior 76 to maintain the substantially constant pressure P1. As the sample 90 cures, the fluid can be extracted from the chamber 80 when the sample 90 expands, and the fluid can be injected into the chamber 80 when the sample 90 shrinks. The pressurization unit 62 can measure the amount of fluid injected/extracted to/from the chamber 80 at any point in time, as the sample 90 cures and present the measurements to the processor 60 for plotting a curve 102 (FIG. 5) which is the complete shrinkage vs. the curing time. The volume of fluid 74 injected/extracted to/from the chamber 80 equals the complete amount of shrinkage (or expansion) of the sample 90 at a particular curing time as the sample 90 cures. It should be understood that the sample 90 will generally shrink during the curing process. However, it is possible that the sample 90 may expand at some point during the curing process. The pressurization unit 62 can maintain a substantially constant pressure P1 in the chamber 80 even when the sample 90 expands.

In preparation for testing a sample 90 of a cement slurry 50 in the UCA 78, a bottom cap 70 can be installed at a bottom of the chamber 80, which can receive the transmitter 82. A tube 88 can be installed in the chamber 80 within the chamber wall 86. The tube 88 can sealingly engage with the bottom cap 70 to prevent fluid flow at the bottom of the tube 88 between an annulus 92 and an interior 76 of the tube 88. The sample 90 can then be poured into the interior 76 of the tube 88 to fill the tube to at or almost at the top of the tube 88. A small space at the top of the sample 90 in the tube 88 can be allowed. This space, if allowed, will be filled with a fluid 74 (such as water) when the top cap 72 is installed at the top of the wall 86 to form the chamber 80. Before the top cap 72 is installed, the fluid 74 can be poured into the annulus 92 to simulate a particular downhole environment. The permeability of the target downhole environment can affect the stresses that build up in the cement sheath 52. If the particular downhole environment is permeable, then the top of the tube 88 may not sealingly engaged with the top cap 72 to allow fluid 74 to flow into the interior 76 of the tube 88 from the annulus 92. However, if the downhole environment is non-permeable, then the tube 88 can be configured to sealingly engage with the top cap 72 and prevent flow of the fluid 74 from the annulus 92 into the interior 76 of the tube 88. Prior to mounting the top cap 72 to the chamber wall 86, additional fluid 74 can be poured into the top of the chamber 80 to ensure that no air bubbles remain in the chamber 80 when the top cap 72 is installed. Additionally, if the sample 90 is isolated in flexible impermeable jacket (such as a very thin rubber like balloon that is substantially impermeable for the duration of test at target temperature T1 and pressure P1) before putting the isolated sample 90 in the chamber 80, the volume exchange (thus complete shrinkage) is said to be measured under impermeable conditions. However, if sample 90 is allowed to physically be in contact with injected/extracted fluid during the volume exchange, the complete shrinkage is said to be measured under permeable conditions. If a target downhole environment has fluids that would be in communication with the cement, then the sample should not be isolated during the test. If the target downhole environment would not have fluids or allow communication of fluids with the cement, then the sample 90 should be isolated during the test.

The fittings 66, 68 can be installed in the top cap 72 to interface the thermocouple 64 and the pressurization unit 62, respectively, to the chamber 80. The ultrasonic receiver 84 can also be installed in the top cap 72. These can be installed in either the top or bottom of the chamber 80, as long as the thermocouple and pressurization units are in communication with the interior 76 of the tube 86, and that the transmitter and receiver are positioned at opposite ends of the tube 86.

Using the UCA 78 of FIG. 3, a sample 90 can be tested to determine its non-plastic state shrinkage (NPSS) at the target downhole environmental conditions. A transit time of the ultrasonic signals 94 through a sample 90 in the interior 76 of the tube 88 can be monitored. The transmitter 82 can transmit the ultrasonic signals 94 into a bottom of the sample 90, which will then travel through the sample 90 to the receiver 84, where the ultrasonic signals 94 are received and the received data is transmitted to the processor 60. The processor 60 can produce the plot curve 120 shown in plot 110 of FIG. 4 by plotting the transit time as a function of the curing time as the sample 90 cures, where time "0" can be when the sample 90 is poured into the tube 88, the chamber 80 is sealed by installing the top cap 72, and the chamber is brought up to the desired temperature T1 and pressure P1.

Figure 4:
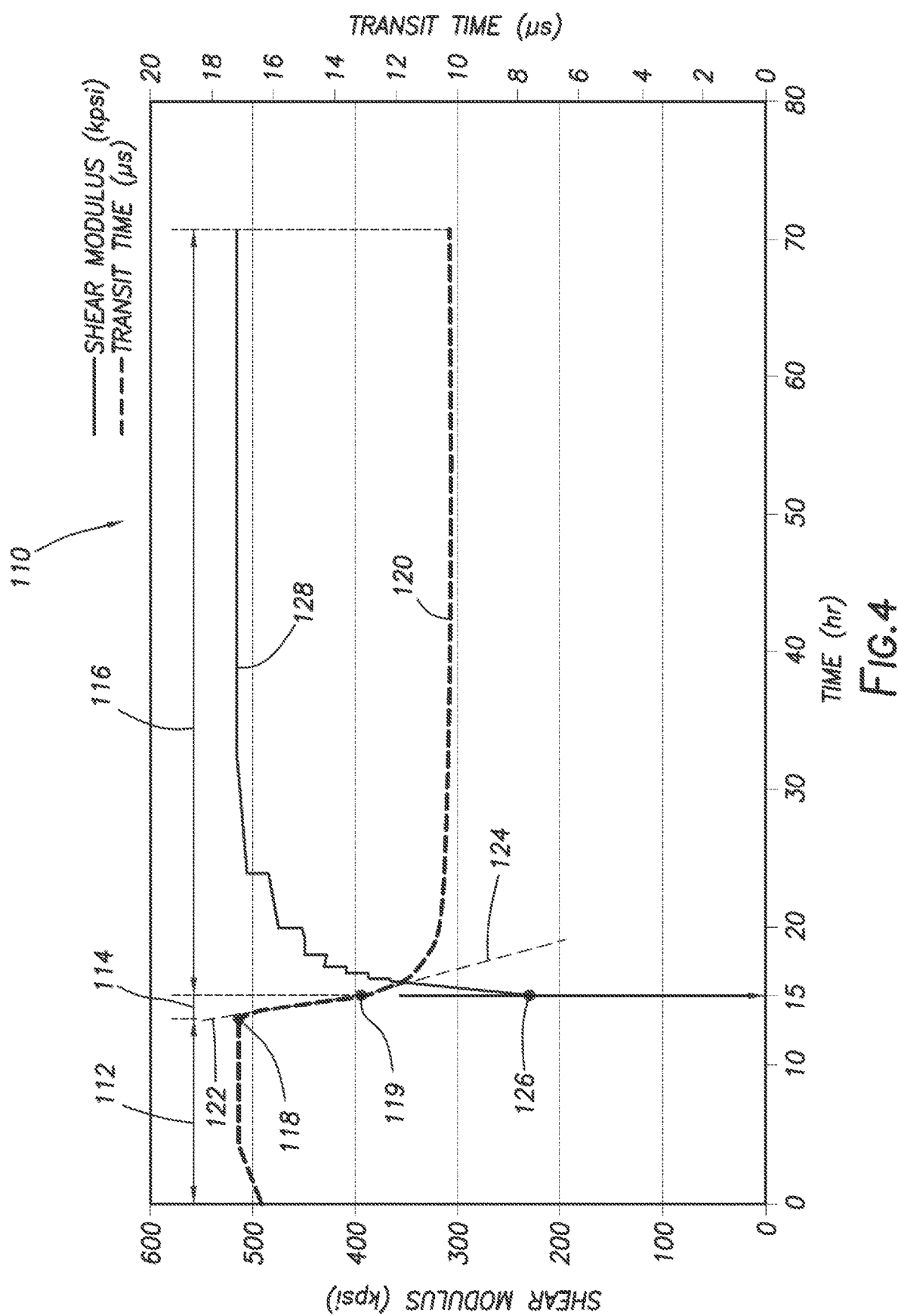
FIG. 4 is a representative plot of transit time and shear modulus measurements of a cement slurry as it goes through a curing process, according to one or more example embodiments.

Referring to FIG. 4, the curve 120 shows a representative plot of the transit time measured for a representative sample 90 as the sample 90 cures in the chamber 80. There are three regions of interest when analyzing the curve 120. Region 112 is the region that extends in time from "zero" time to the point 118 that indicates the beginning of a rapid change in the transit time which can indicate that the sample 90 is shrinking at a rapid rate. This is indicative of the phase of the curing process for the sample 90 that can be referred to as the plastic state shrinkage (PSS) of the sample 90. As stated above, plastic state shrinkage is when the bulk shrinkage equals the complete shrinkage of the sample 90. The rapid decent of the curve 120 in region 114 can have a slope 122 that is a steeper slope than either region 112 or region 116. Also stated above, it is when the non-plastic state shrinkage (NPSS) begins that is of interest, since stresses do not generally build up in the sample 90 when the sample 90 is experiencing the PSS. However, stresses may begin to build in the sample 90 in the NPSS region, which is indicated as region 116 of the curve 120. In analyzing transit time plots, the inventors have discovered that the beginning of the NPSS region 116 can be identified by detecting when the slope of the curve 120 begins to diverge from the slope 122 to a slope 124 shown in FIG. 4. At the point 119 when the curve 120 indicates that the change rate of the transit time is slowing down, thus producing a portion of the curve 120 beginning at point 119 that has a less steep slope (slope 124) when compared to the slope 122 between points 118 and 119. At point 119 in the curing time of the sample 90, the sample 90 begins to experience NPSS, which can cause stresses to build in the sample 90. As the curing time continues past point 119, the shrinkage of the sample 90 continues to decrease, as seen in region 116 and indicated by the leveling out of the transit time curve 120.

Now that the point 119 has been identified for this representative sample 90, the curing time at point 119 (which is shown to be 15 hrs in FIG. 4) can be correlated to a plot of the shrinkage of the sample 90 to determine the actual shrinkage that has occurred during the NPSS region 116. The UCA 78 simultaneously monitors the transit time and the shrinkage of the sample 90. This ensures that both tests are performed with identical conditions for the sample 90, which may not be the case with the current methods that perform the two tests to determine bulk and total shrinkage.

Figure 5:
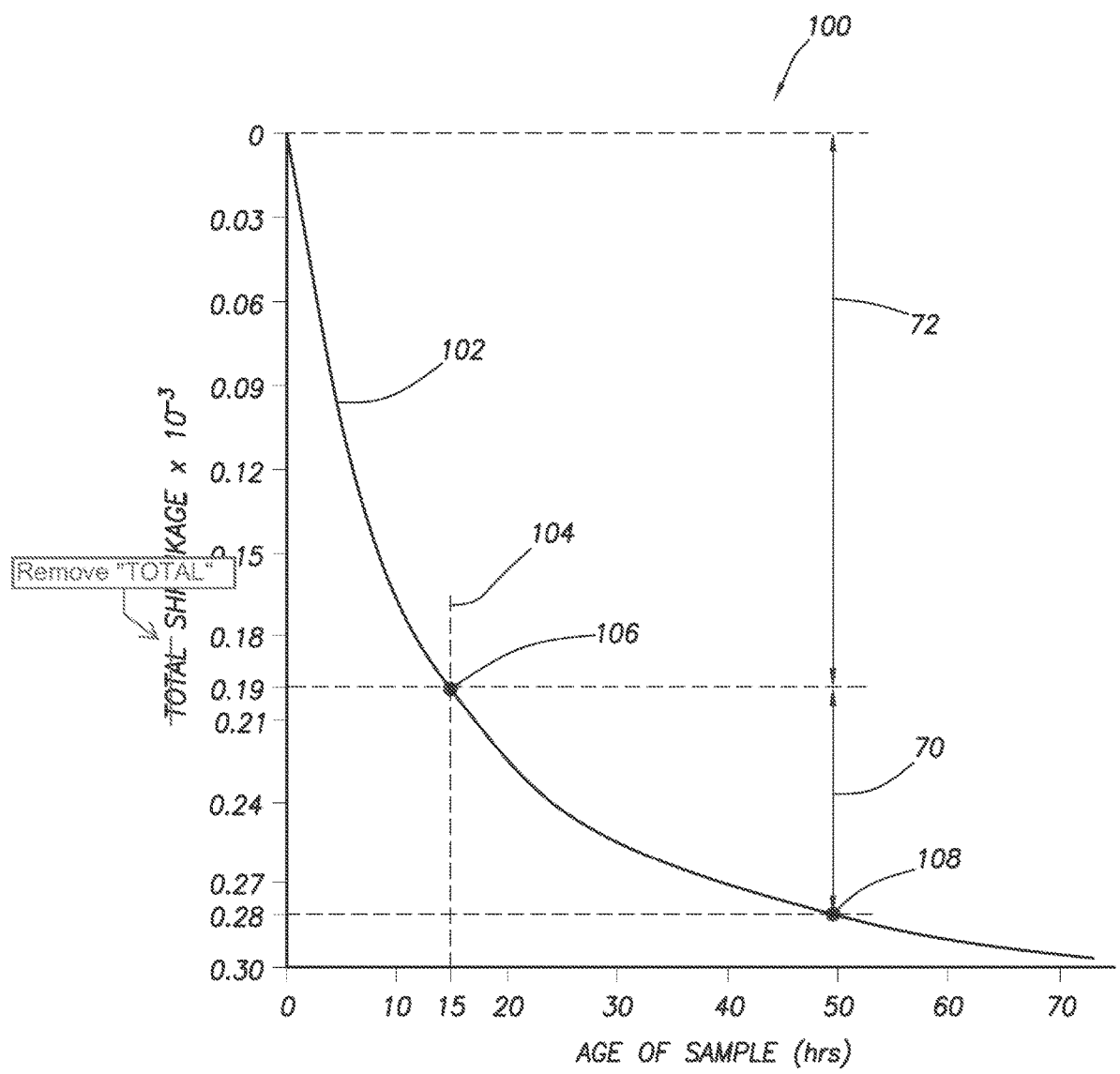
FIG. 5 is a representative plot of shrinkage measurements of the cement slurry as it goes through a curing process, according to one or more example embodiments.

Referring to FIG. 5, a representative curve 102 of plot 100 is shown that displays a plot of the shrinkage amount as a function of the curing time of the sample 90. The shrinkage amount can be determined from the detected volume, by comparing the detected volume to an initial volume of the sample 90 which is taken at the beginning of the test. The initial volume of the sample 90 can be determined by pouring a known volume of cement slurry 50 into the tube 88. The initial volume of the sample 90 can also be calculated by determining the diameter of the tube 88 and the height of the sample 90 within the tube 88. This initial volume can then be used to determine a shrinkage amount (or ratio) of the sample 90 by dividing the detected volume by the initial volume. A percentage of shrinkage can be determined by multiplying the shrinkage amount (or ratio) by 100 to yield the percentage. Taking the curing time associated with point 119 in FIG. 4, and finding the point 106 on the curve 102 that intersects the curing time (i.e. 15 hrs in this example), then the amount of shrinkage that is attributed to the PSS regions 112, 114, and the amount of shrinkage that is attributed to the NPSS region 116 can be determined. Therefore, to determine the amount of shrinkage that occurred during the NPSS region 116, for example, at point 108 of FIG. 5, the shrinkage amount at point 106 (which is $0.19 \times 10^{}-3$) can be subtracted from the shrinkage amount at point 108 (which is $0.28 \times 10^{}-3$) and produce a shrinkage amount of $0.09 \times 10^{}-3$, which is the shrinkage amount in this example that occurred during the NPSS region 116. This value can then be converted to a percentage value (for example $9.0 \times 10^{}-3\%$), which can be input into the simulation tool 46 to calculate the predicted stresses that may occur in a cement sheath 52 if a cement slurry of the composition of the sample 90 is flowed into the annulus 54 in the wellbore 12 to secure the casing 34 in the wellbore 12. If these calculated stresses appear to be unacceptable (such as if these stresses pose a risk of the cement sheath mechanically failing), then the composition of the sample 90 can be modified and another sample 90 with the modified composition can again be tested in the UCA to produce new NPSS data. The new NPSS data can be input into the simulation tool 46, which can again determine predicted stresses that may occur in the cement sheath 52 if a cement slurry with the modified composition were used.

Referring back to FIG. 4, it can be seen that a test to determine a shear modulus for the sample 90 can be ran and the shear modulus data correlates very well with the point 119 that marks the beginning of the NPSS region 116. The shear modulus test can be performed on a second sample 90 of the same composition as the first sample 90 that was tested in the UCA, at the same temperature T1 and pressure P1. As the second sample 90 cures, the shear modulus test (using a shear wave) is not able to calculate a shear modulus until the solidity of the second sample 90 is at the beginning of the NPSS region 116, which allows the second sample to develop a shear modulus, since the sample is no longer in liquid form. A solid structure extends through the second sample 90 that prevents further PSS, as in region 114. As can be seen, the beginning point 126 of the shear modulus curve 128 is generally at the same curing time as point 119 on the curve 120. Curve 128 represents the shear modulus plotted as a function of the curing time of the second sample 90. Since the first and second samples 90 are of the same composition, the solidity of both samples form at basically the same time and the NPSS region 116 can begin at the same curing time as the beginning of the shear modulus curve 128. It should be understood that measuring the shear modulus of a sample is not required. It has been included here as a point of discussion and comparison, but is not necessary to calculate the NPSS shrinkage in cement samples 90 using the principles of the current disclosure.

Figure 6:
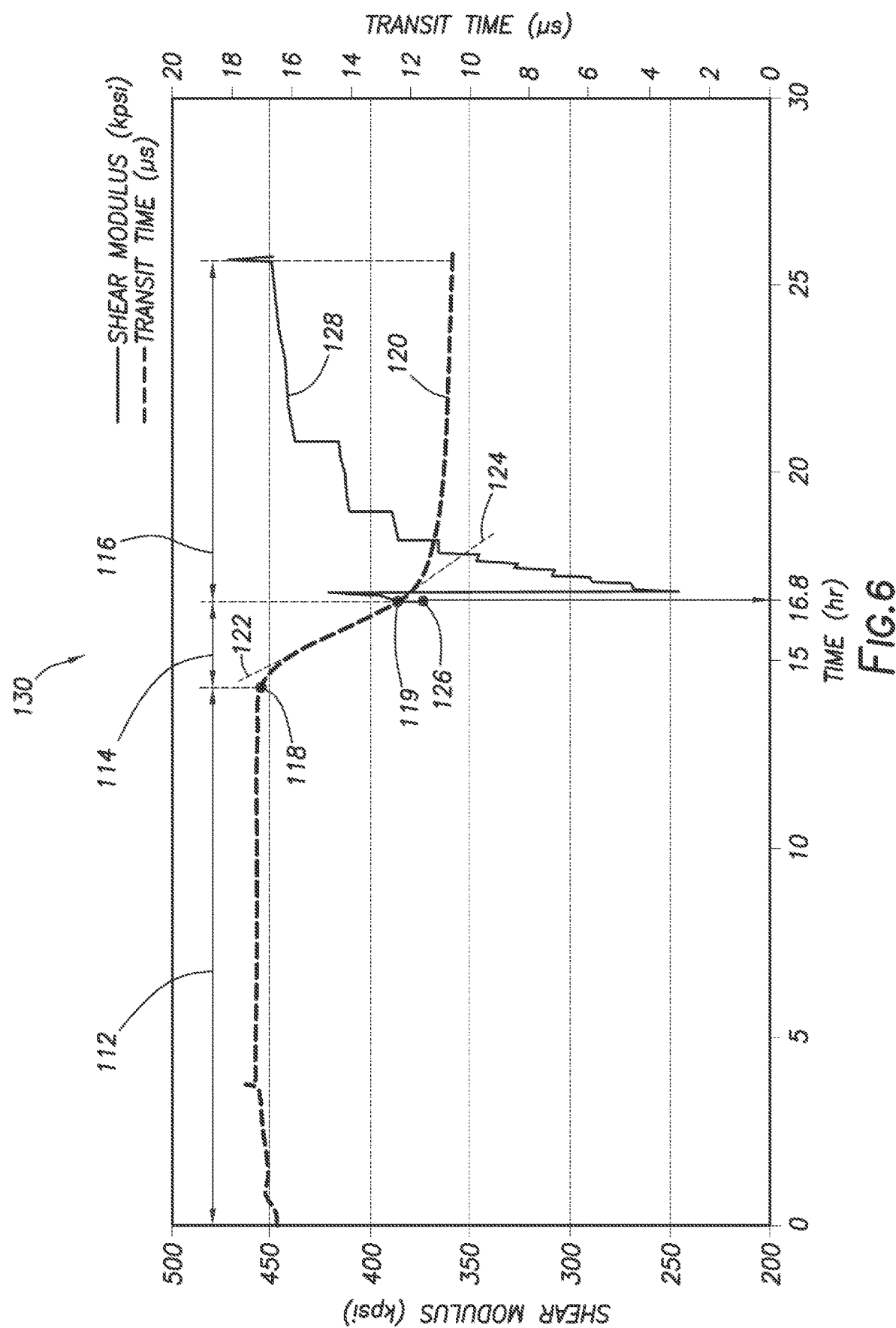
FIG. 6 is a representative plot of transit time and shear modulus measurements of another cement slurry as it goes through a curing process, according to one or more example embodiments.

Referring to FIG. 6, a new sample 90 with a different composition was tested in the UCA 78 and the transit time for the new sample 90, as it was cured, was recorded by the processor 60 and displayed to the display unit 61. The new curve 120 has some differences from the curve 120 in FIG. 4. The new curve 120 still has the three regions 112, 114, 116, with the PSS occurring in the regions 112 and 114. Region 114 begins at the point 118 and ends at the point 119, where the slope of the curve 120 begins to diverge from the slope 122 in the region 114. Point 119 in this example is 16.8 hrs instead of 15 in the previous example. To calculate the NPSS for this new sample 90, the point 119 (i.e. 16.8 hrs) is correlated to another plot of shrinkage vs. the curing time. Finding the intersection of the curing time (i.e. 16.8 hrs) with a new curve 102 can yield the shrinkage due to PSS in the new sample and this value can be subtracted from any shrinkage value on the curve 102 after the curing time 16.8 hrs to yield the NPSS for the new sample 90. The new NPSS can again be input into the simulation tool 46 to determine the expected stresses that may occur with a cement slurry of the composition of the new sample 90. Additionally, another shear modulus test was performed with another sample 90 of the new composition. As before, the beginning point 126 of the shear modulus curve 128 begins basically at the same curing time (i.e. point 119) for this additional example of a cement slurry 50.

Figure 7:
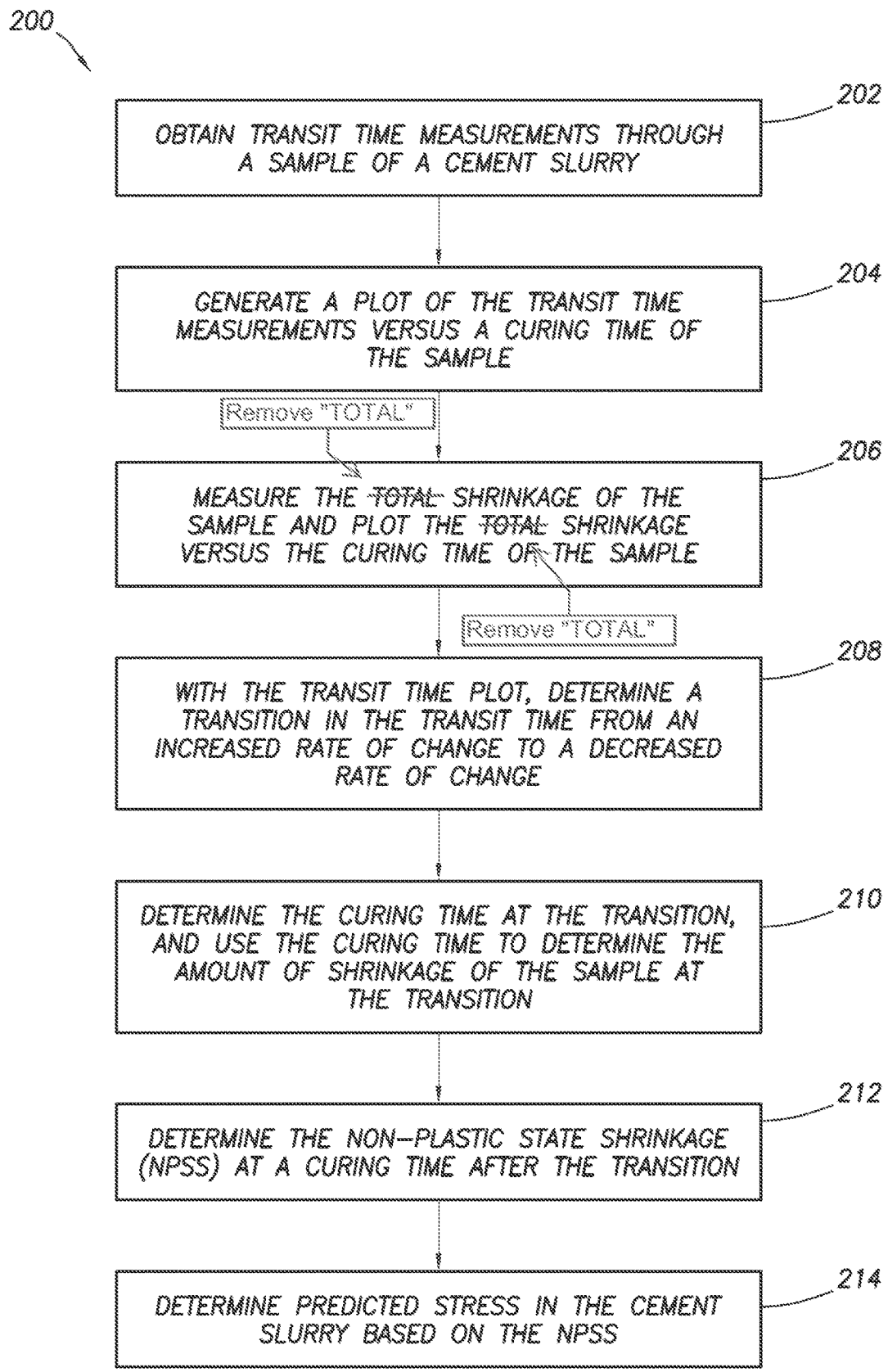
FIG. 7 is a representative flow chart of a method for estimating stress in the cement slurry in a downhole environment based on a non-plastic state shrinkage characteristic of the cement slurry, according to one or more example embodiments.

FIG. 7 shows a representative flow diagram of a method 200 for estimating stress in a cement slurry 50 in a downhole environment based on a non-plastic state shrinkage (NPSS) characteristic of the cement slurry 50, which is determined prior to the cement slurry being installed into the wellbore 12. The method can include an operation 202 that uses the UCA 78, as described above, to measure the transit time of a sample 90 of a cement slurry 50 as the sample 90 cures. The transit time data can be generated by the controller 60 controlling a transmitter 82 to transmit ultrasonic signals 94 through the sample 90, which can be received by a receiver 84 after traveling through the sample 90. In operation 204, the controller 60 can receive the transit time data, and process the data to format it into a plot curve 120 that has the transit time data plotted as a function of the curing time. The plot curve 120 can be displayed by the display unit 61 as plot 110. In operation 206, the UCA 78 can also measure the shrinkage of the sample 90 as it cures. The UCA can format the data and/or the processor 60 can format the shrinkage measurements into a plot curve 102 that has the shrinkage data plotted as a function of the curing time. The plot curve 102 can be displayed by the display unit 61 as plot 100.

In operation 208, a transition in the transit time shown in plot curve 120 can be identified, where the transition is where the transit time plot changes from an increased rate of change to a decreased rate of change. This transition is a point on the curve 120 that correlates to a curing time. At operation 210, the curing time is indicated on the plot curve 102 that plots the shrinkage of the sample 90 as it cures. The shrinkage is plotted as a function of the curing time. Therefore, knowing the curing time for the transition point (i.e. point 119 in FIGS. 4 and 6), the point on the shrinkage plot curve 102 that corresponds to the curing time of point 119 of the curve 120 is also known. This gives the value of the plastic state shrinkage (PSS). In operation 212, the PSS amount can subtracted from complete shrinkage amount that corresponds to any point on the curve 102 after the curing time of point 119 to yield the NPSS of the point after the curing time of the point 119. In operation 214, the NPSS values can be input into the simulation tool 46, which can use the NPSS values to calculate the predicted stresses that can develop in a cement slurry 50 that has the same composition as the sample 90. If the predicted stresses appear to be unacceptable, then the composition of the cement slurry 50 can be modified, with a sample 90 of the modified cement slurry being tested again to produce new NPSS data, which can be put back into the simulation tool 46 to calculate predicted stresses again. When the stresses appear to be acceptable from the simulation tool results, then the cement slurry 50 with the desired composition can be installed in a wellbore 12 with the particular environment that was simulated by the simulation tool 46.

Thus, a method for determining a non-plastic state shrinkage (NPSS) characteristic of a cement slurry is provided, which can include the operations of filling a container with the cement slurry, positioning a transmitter at an end of the container, positioning a receiver at an opposite end of the container, transmitting an ultrasonic signal through the cement slurry from the transmitter to the receiver, recording a transit time of the ultrasonic signal through the cement slurry as the cement slurry cures, plotting a first plot of the transit time vs. a curing time of the cement slurry, maintaining the cement slurry at a constant pressure by injecting a fluid into the container, thereby compensating for shrinkage of the cement slurry as the cement slurry cures, detecting a volume of the fluid injected into the container as the cement slurry cures, plotting a second plot of the detected volume vs. the curing time of the cement slurry, determining a first slope of the first plot that indicates an increased rate of change in the transit time and a second slope of the first plot that indicates a decreased rate of change in the transit time, determining a first curing time at which the first slope intersects the second slope, determining the detected volume at the first curing time based on the second plot, and determining a change in the detected volume from the first curing time to a second curing time, wherein the second curing time is after the first curing time.

For any of the foregoing embodiments, the method may include any one of the following elements, alone or in combination with each other:

The operations can also include determining a percentage of shrinkage of the cement slurry based on comparing an initial volume of the cement slurry to the detected volume, and/or determining a percentage of shrinkage of the cement slurry during the NPSS based on comparing an initial volume of the cement slurry to the change in the detected volume and calculating a stress on the cement slurry based on the percentage of shrinkage of the cement slurry that occurred during the NPSS.

The operations can also include maintaining the cement slurry at the constant pressure and a constant temperature, where the constant pressure and temperature can be representative of a downhole environment. The container can be a tube positioned within a chamber with an annulus between the chamber and the tube, and the constant pressure and temperature can be maintained within the chamber. The tube can be filled with the cement slurry and the annulus can be filled with a fluid. The cement slurry can be in fluid communication with the fluid in the annulus as the cement slurry cures, which can simulate curing of the cement slurry in a permeable downhole environment. Alternatively, the cement slurry can be isolated from the fluid in the annulus as the cement slurry cures, which can simulate curing of the cement slurry in a non-permeable downhole environment.

Another method of estimating a stress in a cement slurry in a downhole environment is provided, which can include the operations of transmitting an ultrasonic signal through a sample of the cement slurry, recording a transit time (which is a time required for the ultrasonic signal to pass through the sample) as the sample cures, plotting a first plot of the transit time vs. a curing time of the cement slurry, maintaining the sample at a constant pressure by injecting a fluid into a chamber that contains the sample, thereby compensating for shrinkage of the sample as the sample cures, detecting a volume of the fluid injected into the chamber as the sample cures, plotting a second plot of the detected volume vs. the curing time of the sample, determining a first curing time at which a first slope of an increased rate of change in the transit time changes to a second slope of a decreased rate of change in the transit time, determining the detected volume at the first curing time based on the second plot, and determining a change in the detected volume from the first curing time to a second curing time, wherein the second curing time is after the first curing time.

For any of the foregoing embodiments, the method may include any one of the following elements, alone or in combination with each other:

The operations can also include calculating a stress on the sample based on the change of the detected volume, thereby estimating the stress in the cement slurry when it is used in the downhole environment, maintaining the sample at the constant pressure and a constant temperature, wherein the constant pressure and temperature can be representative of the downhole environment. A tube can be positioned in the chamber with an annulus between the chamber and the tube, and the constant pressure and a constant temperature can be maintained within the chamber. The tube can be filled with the sample and the annulus can be filled with a fluid. The sample can be in fluid communication with the fluid in the annulus as the sample cures, which can simulate curing of the sample in a permeable downhole environment. Alternatively, the sample can be isolated from the fluid in the annulus as the sample cures, which can simulate curing of the sample in a non-permeable downhole environment, and a percentage of shrinkage of the sample can be determined based on comparing an initial volume of the sample to the detected volume.

The operations can also include determining a percentage of shrinkage of the sample during the NPSS based on comparing an initial volume of the sample to the change in the detected volume, and calculating an estimated stress in the cement slurry in the downhole environment based on the percentage of the shrinkage of the sample that occurred during the NPSS Furthermore, the illustrative methods described herein may be implemented by a system comprising processing circuitry that can include a non-transitory computer readable medium comprising instructions which, when executed by at least one processor of the processing circuitry, causes the processor to perform any of the methods described herein.

Although various embodiments have been shown and described, the disclosure is not limited to such embodiments and will be understood to include all modifications and variations as would be apparent to one skilled in the art. Therefore, it should be understood that the disclosure is not intended to be limited to the particular forms disclosed; rather, the intention is to cover all modifications, equivalents, and alternatives falling within the spirit and scope of the disclosure as defined by the appended claims.

The invention claimed is:

1. A method of determining a non-plastic state shrinkage (NPSS) characteristic of a cement slurry, the method comprising:
    filling a container with the cement slurry;
    positioning a transmitter at an end of the container;
    positioning a receiver at an opposite end of the container;
    transmitting an ultrasonic signal through the cement slurry from the transmitter to the receiver;
    recording a transit time of the ultrasonic signal through the cement slurry as the cement slurry cures;
    plotting a first plot of the transit time vs. a curing time of the cement slurry;

maintaining the cement slurry at a constant pressure by injecting a fluid into the container, thereby compensating for shrinkage of the cement slurry as the cement slurry cures;

detecting a volume of the fluid injected into the container as the cement slurry cures;

plotting a second plot of the detected volume vs. the curing time of the cement slurry;

determining a first slope of the first plot that indicates an increased rate of change in the transit time and a second slope of the first plot that indicates a decreased rate of change in the transit time;

determining a first curing time at which the first slope intersects the second slope;

determining the detected volume at the first curing time based on the second plot; and determining a change in the detected volume from the first curing time to a second curing time, wherein the second curing time is after the first curing time.

2. The method of claim 1, further comprising determining a percentage of shrinkage of the cement slurry based on comparing an initial volume of the cement slurry to the detected volume.

3. The method of claim 1, further comprising determining a percentage of shrinkage of the cement slurry during the NPSS based on comparing an initial volume of the cement slurry to the change in the detected volume.

4. The method of claim 3, further comprising calculating a stress on the cement slurry based on the percentage of shrinkage of the cement slurry that occurred during the NPSS.

5. The method of claim 1, further comprising maintaining the cement slurry at the constant pressure and a constant temperature, wherein the constant pressure and temperature are representative of a downhole environment.

6. The method of claim 5, wherein the container is a tube positioned within a chamber with an annulus between the chamber and the tube, and the constant pressure and temperature are maintained within the chamber.

7. The method of claim 6, wherein the tube is filled with the cement slurry and the annulus is filled with a fluid.

8. The method of claim 7, wherein the cement slurry is in fluid communication with the fluid in the annulus as the cement slurry cures, which simulates curing of the cement slurry in a permeable downhole environment.

9. The method of claim 7, wherein the cement slurry is isolated from the fluid in the annulus as the cement slurry cures, which simulates curing of the cement slurry in a non-permeable downhole environment.

10. A method of estimating a stress in a cement slurry in a downhole environment, the method comprising:

transmitting an ultrasonic signal through a sample of the cement slurry;

recording a transit time, which is a time required for the ultrasonic signal to pass through the sample, as the sample cures;

plotting a first plot of the transit time vs. a curing time of the cement slurry;

maintaining the sample at a constant pressure by injecting a fluid into a chamber that contains the sample, thereby compensating for shrinkage of the sample as the sample cures;

detecting a volume of the fluid injected into the chamber as the sample cures;

plotting a second plot of the detected volume vs. the curing time of the sample;

determining a first curing time at which a first slope of an increased rate of change in the transit time changes to a second slope of a decreased rate of change in the transit time;

determining the detected volume at the first curing time based on the second plot; and determining a change in the detected volume from the first curing time to a second curing time, wherein the second curing time is after the first curing time.

11. The method of claim 10, further comprising calculating a stress on the sample based on the change of the detected volume, thereby estimating the stress in the cement slurry when it is used in the downhole environment.

12. The method of claim 10, further comprising maintaining the sample at the constant pressure and a constant temperature, wherein the constant pressure and temperature are representative of the downhole environment.

13. The method of claim 10, wherein a tube is positioned in the chamber with an annulus between the chamber and the tube, and the constant pressure and a constant temperature are maintained within the chamber.

14. The method of claim 13, wherein the tube is filled with the sample and the annulus is filled with a fluid.

15. The method of claim 14, wherein the sample is in fluid communication with the fluid in the annulus as the sample cures, which simulates curing of the sample in a permeable downhole environment.

16. The method of claim 14, wherein the sample is isolated from the fluid in the annulus as the sample cures, which simulates curing of the sample in a non-permeable downhole environment.

17. The method of claim 10, further comprising determining a percentage of shrinkage of the sample based on comparing an initial volume of the sample to the detected volume.

18. The method of claim 10, further comprising determining a percentage of shrinkage of the sample during the NPSS based on comparing an initial volume of the sample to the change in the detected volume.

19. The method of claim 18, further comprising calculating an estimated stress in the cement slurry in the downhole environment based on the percentage of the shrinkage of the sample that occurred during the NPSS.

\* \* \* \* \*